United States Patent
Michel et al.

(10) Patent No.: US 7,935,049 B2
(45) Date of Patent: May 3, 2011

(54) MEDICAL INSTRUMENT, IN PARTICULAR URETERO-RENOSCOPE

(75) Inventors: Maurice Stephan Michel, Mannheim (DE); Peter Eisenkolb, Tuttlingen (DE); Andreas Efinger, Rietheim (DE)

(73) Assignee: Karl Storz GmbH & Co. KG (DE)

( * ) Notice: Subject to any disclaimer, the term of this patent is extended or adjusted under 35 U.S.C. 154(b) by 520 days.

(21) Appl. No.: 11/233,159

(22) Filed: Sep. 22, 2005

(65) Prior Publication Data

US 2006/0089534 A1   Apr. 27, 2006

(30) Foreign Application Priority Data

Oct. 25, 2004   (DE) .................... 20 2004 016 621 U

(51) Int. Cl.
*A61B 1/00* (2006.01)
*A61B 1/307* (2006.01)
(52) U.S. Cl. .................. 600/128; 600/105; 600/135
(58) Field of Classification Search .............. 600/105, 600/127, 128, 129, 130, 153, 156, 158, 104, 600/135, 155, 157
See application file for complete search history.

(56) References Cited

U.S. PATENT DOCUMENTS

| | | | | |
|---|---|---|---|---|
| 2,487,498 A * | 11/1949 | Wallace | .................... | 600/153 |
| 3,496,930 A * | 2/1970 | Wappler | .................... | 600/135 |
| 4,369,768 A * | 1/1983 | Vukovic | .................... | 600/123 |
| 4,557,255 A * | 12/1985 | Goodman | .................... | 600/104 |
| 4,911,148 A | 3/1990 | Sosnowski et al. | .............. | 128/6 |
| 5,031,603 A * | 7/1991 | Gautier et al. | ................ | 600/135 |
| 5,170,774 A * | 12/1992 | Heckele | .................... | 600/128 |
| 5,505,687 A * | 4/1996 | Walther et al. | ................ | 600/104 |
| 5,536,234 A * | 7/1996 | Newman | .................... | 600/104 |
| 5,685,824 A * | 11/1997 | Takei | .................... | 600/135 |
| 5,823,940 A * | 10/1998 | Newman | .................... | 600/105 |
| 6,458,076 B1 * | 10/2002 | Pruitt | .................... | 600/146 |
| 6,547,724 B1 | 4/2003 | Soble et al. | .................. | 600/156 |
| 6,616,600 B2 | 9/2003 | Pauker | .................... | 600/128 |
| 7,238,153 B2 * | 7/2007 | Moriyama | .................... | 600/127 |
| 2004/0204629 A1 | 10/2004 | Knapp | .................... | 600/156 |
| 2004/0249246 A1 * | 12/2004 | Campos | .................... | 600/160 |
| 2005/0065398 A1 * | 3/2005 | Adams | .................... | 600/105 |

OTHER PUBLICATIONS

Karl Storz Endoskope Catalogue "Urologie". 7th Edition, Jan. 2003 Section 10 (4 pages).

* cited by examiner

*Primary Examiner* — Linda C Dvorak
*Assistant Examiner* — Alireza Nia
(74) *Attorney, Agent, or Firm* — St. Onge Steward Johnston & Reens LLC

(57) ABSTRACT

A medical instrument in particular a uretero-renoscope has a proximal head part and an elongate thin shaft for introduction into a small diameter elongate hollow organ. An instrument channel and at least one further channel is disposed within the shaft. The instrument channel is arranged centrally in the shaft.

5 Claims, 1 Drawing Sheet

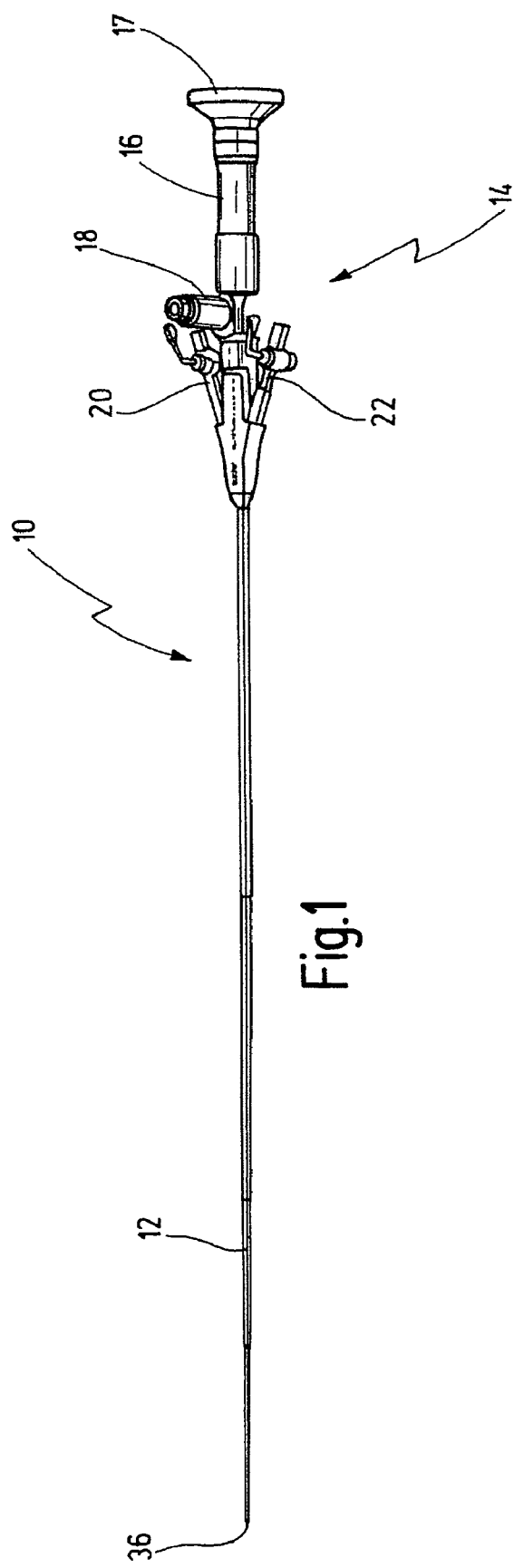
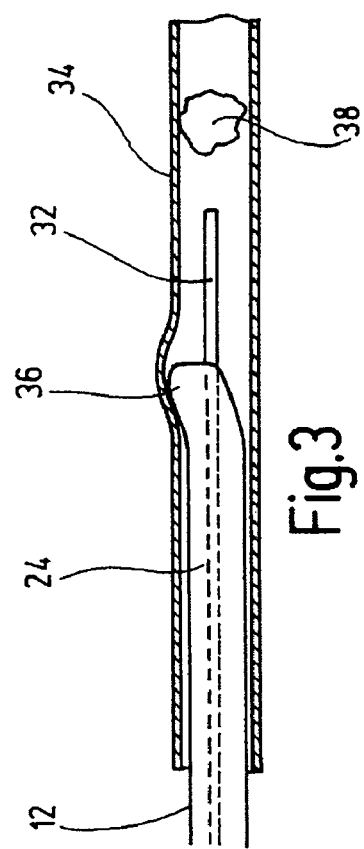
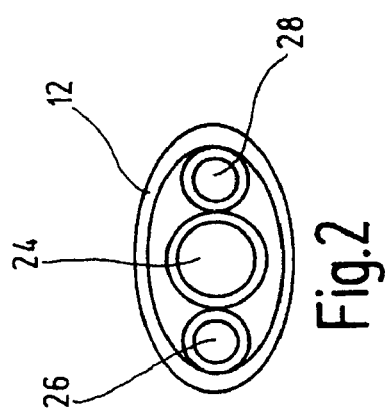

MEDICAL INSTRUMENT, IN PARTICULAR URETERO-RENOSCOPE

This application claims priority of German Patent Application No. 20 2004 016 621.6 filed on Oct. 25, 2004.

BACKGROUND OF THE INVENTION

The invention relates to a medical instrument, in particular a uretero-renoscope, with a proximal head part and with an elongate thin shaft for introduction into elongate hollow organs, in particular into a ureter.

Medical instruments of this kind are known, for example, from the Applicant's catalogue "Urologie", 7th edition, 1/2003, section 10 "Uretero-Renoskope".

For their application in urology, instruments of this kind are intended to be able to be inserted into hollow organs in the form of ureters. For this purpose, they have an extremely long and thin shaft, for example with a length in the region of up to 50 cm and with a diameter of 2 to 5 mm.

Several channels are present in the shaft itself. One channel serves as instrument channel to allow an instrument, for example an ultrasound probe, to be conveyed through the shaft, for example in order to crush a stone located in a ureter.

Moreover, in order to monitor these procedures, there is a further channel for an optical system consisting of light guides and image guides, and at least one suction and irrigation channel. In some designs, the suction channel and irrigation channel are separate, so that there are four channels in total. These channels are packed as closely as possible together in the shafts, said shafts accordingly having oval, rounded or elliptic cross sections, or cross sections flattened on side, as is evident from the catalogue mentioned above.

A common feature of all designs is that the instrument channel is arranged laterally.

In practical use, it has now been found that there is a risk that instruments pushed out distally via the instrument channel may damage the wall of the ureter. Since these instruments are extremely thin, they have a certain flexibility. The risk of damage arises upon lateral deflection and penetration into the wall of the ureter, especially in the case of an instrument pushed out past the distal tip of the shaft.

It is therefore an object of the present invention to rectify this situation and provide an instrument which largely avoids such damage.

SUMMARY OF THE INVENTION

According to the invention, the object is achieved by the fact that the instrument channel is arranged centrally in the shaft.

Within the context of the present invention, centrally means that the instrument channel is arranged such that, in radial directions, it is spaced apart as far as possible from the outside of the shaft. The instrument channel can in this case lie centrally and exactly coaxially in the longitudinal axis. Depending on its geometric cross-sectional shape, it can also be offset slightly, the important thing being that on all sides it is at a distance from the shaft circumference.

If an instrument is now pushed through this central channel, it exits the distal end of the shaft with an orientation in which the instrument is in each case at a possible longest distance from the inside face of the hollow organ, that is to say of the ureter, so that a risk of injury is greatly reduced.

In a further embodiment of the invention, the shaft is somewhat laterally enlarged in its distal end section.

This enlargement provides a certain radial widening of the elongate hollow organ, for example the ureter, by the distal end section, at which distal end an instrument conveyed through the central instrument channel comes out. The risk of a damage of the inner wall of the elongate hollow organ is further reduced, since the radial distance between the instrument coming out of the distal end of the central instrument channel is extended. Due to the central arrangement of the instrument channel the risk of damaging the inner wall is reduced in all radial directions viewed from a center line of the instrument channel.

The lateral enlargement of the shaft can be performed by laterally cranking or bending of the distal end of the shaft.

In a further embodiment of the invention, the further channels are in each case arranged alongside or around the central instrument channel.

This measure has the advantage that not only can the central instrument channel have the optimal or maximum distance from the outside of the shaft, but also the channels arranged around the central channel allow further necessary measures to be taken, for example irrigation measures, in which case the probe lying centrally can, for example, be flushed free of impurities that have attached to it.

In a further embodiment of the invention, the at least one further channel includes a suction and irrigation channel or a suction channel and an irrigation channel and/or an optical system.

Depending on the configuration, there are therefore three or four channels arranged around the central channel.

For a compact design, and depending on the cross-sectional profile of the shaft, the central instrument channel can be round, or flattened in the lateral direction, or of some other shape ensuring that the other shafts can bear closely against it in order to save as much space as possible.

All constructions have in common the fact that the instrument channel is arranged centrally.

It will be appreciated that the features mentioned above and those still to be explained below can be used not only in the stated combinations, but also in other combinations or singly, without departing from the scope of the present invention.

BRIEF DESCRIPTION OF THE DRAWINGS

The invention is described and explained in greater detail below on the basis of a selected illustrative embodiment and with reference to the attached drawings, in which:

FIG. 1 shows a uretero-renoscope,

FIG. 2 shows a plan view of the distal end of the uretero-renoscope from FIG. 1, and FIG. 3 shows a highly schematic representation of a hollow organ in the form of a ureter in which a uretero-renoscope according to the invention is inserted, and with an instrument pushed through the shaft.

DETAILED DESCRIPTION OF PREFERRED EMBODIMENT

A medical instrument 10 shown in FIG. 1 is in the form of a uretero-renoscope.

The medical instrument 10 has an elongate shaft 12 and a head part 14. The head part 14 accommodates an optical system 16 which ends in an eyepiece cup 17. A light guide is attached via a lateral connector piece 18.

There are also two further connector pieces 20 and 22 which are each provided with a cock (not specifically shown here), for example for guiding irrigation fluids into the shaft 12 or for suctioning these fluids off again through the shaft 12.

The shaft 12 has a length of approximately 35 cm and a diameter of 3.5 mm.

The cross section of the shaft 12 is circular along most of its length; in the distal end area the cross section is oval or flattened. From the plan view of the distal end 36 of the shaft 12 in FIG. 2, it will be seen that an instrument channel 24 is arranged centrally therein, in the present case centrally and coaxially. Alongside the central instrument channel 24 there are an optics channel 26 and also a suction and irrigation channel 28.

FIG. 3 shows how the shaft 12 of the instrument 10 is inserted into a hollow organ in the form of a ureter 34 in which a kidney stone 38 is located.

In a manner known per se, the distal end 36 of the shaft is slightly offset, cranked or bent in order to permit atraumatic insertion into the ureter 34 and to enlarge the ureter 34.

A probe 32 is pushed through the central instrument channel 24 and is used to crush the kidney stone 38.

It will be seen from FIG. 3 that, by virtue of the central arrangement of the instrument channel 24, an instrument 32 which is pushed through the latter and out of the distal end is spaced apart in all radial directions from the inside wall of the ureter 34, with the result that damage to this ureter wall is avoided even when the probe 32 deflects sidewards.

This probe can now be advanced centrally to the kidney stone 38 and applied to the latter in order to then crush it.

What is claimed is:

1. Medical instrument having
a head part at its proximal end, and single elongate thin shaft for introduction in small diameter elongate hollow organs, said shaft comprising a cross-section that is circular along most of its length and oval in its distal end area, an instrument channel, and at least two but not more than three further channels arranged alongside and around said instrument channel, wherein said instrument channel is arranged centrally in said shaft such that, in radial directions, said instrument channel is spaced apart as far as possible from a circumference of said shaft and is on all sides at a distance from an inner circumference of said shaft, and wherein said shaft is laterally enlarged in the distal end area by being bent at said distal end area.

2. Medical instrument of claim 1, wherein said at least two but not more than three further channels are selected from the group consisting of a suction channel, an irrigation channel, a combined suction/irrigation channel and an optical system channel.

3. Medical instrument of claim 1, wherein said instrument is designed as a uretero-renoscope, and said elongate hollow organ is a ureter.

4. Medical instrument of claim 1, wherein there are two further channels arranged alongside and around said instrument channel.

5. Medical instrument of claim 1, wherein there are three further channels arranged alongside and around said instrument channel.

* * * * *